(12) United States Patent
Mori

(10) Patent No.: US 7,662,988 B2
(45) Date of Patent: Feb. 16, 2010

(54) ESTER COMPOUND AND ITS USE

(75) Inventor: Tatsuya Mori, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 37 days.

(21) Appl. No.: 12/223,127

(22) PCT Filed: Jan. 16, 2007

(86) PCT No.: PCT/JP2007/050859

§ 371 (c)(1),
(2), (4) Date: Jul. 23, 2008

(87) PCT Pub. No.: WO2007/083781

PCT Pub. Date: Jul. 26, 2007

(65) Prior Publication Data

US 2009/0170936 A1 Jul. 2, 2009

(30) Foreign Application Priority Data

Jan. 23, 2006 (JP) ............................. 2006-013482

(51) Int. Cl.
*C07C 229/00* (2006.01)
*A61K 31/275* (2006.01)
*A01N 37/34* (2006.01)
(52) U.S. Cl. ........................................ 560/38; 514/521
(58) Field of Classification Search ........................ None
See application file for complete search history.

(56) References Cited

U.S. PATENT DOCUMENTS 5,530,022 A 6/1996 Babin et al.
6,908,945 B2 6/2005 Mori
2003/0195119 A1 10/2003 Mori

FOREIGN PATENT DOCUMENTS

| EP | 0 196 156 | 10/1986 |
| EP | 0 638 543 | 2/1995 |
| JP | 61-207361 | 9/1986 |

OTHER PUBLICATIONS

International Search Report mailed Mar. 22, 2007 in the International (PCT) Application PCT/JP2007/050859 corresponding to the present U.S. Application.
English version of PCT Written Opinion issued Mar. 22, 2007 in connection with the International (PCT) Application PCT/JP2007/050859 of which the present application is the U.S. National Stage.

*Primary Examiner*—Yong S Chong
*Assistant Examiner*—Jody L Karol
(74) *Attorney, Agent, or Firm*—Wenderoth, Lind & Ponack, L.L.P.

(57) ABSTRACT

An ester compound represented by the formula (1):

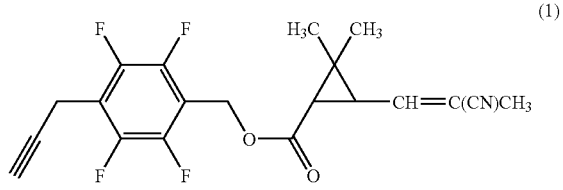

has excellent pest controlling activity and is useful as an active ingredient for a pest controlling agent.

3 Claims, No Drawings

ESTER COMPOUND AND ITS USE

TECHNICAL FIELD

The present invention relates to an ester compound and its use.

BACKGROUND ART

EP 0196156 A1 describes certain fluorobenzyl ester compounds as an active ingredient of insecticides. However, the insecticidal activity of the fluorobenzyl ester compounds is not necessarily sufficient.

DISCLOSURE OF THE INVENTION

As a result of the intensive study to find a compound having excellent pest controlling activity, the present inventor has found that a compound represented by the formula (1) has excellent pest controlling activity, and has completed the present invention.

That is, the present invention provides an ester compound represented by the formula (1):

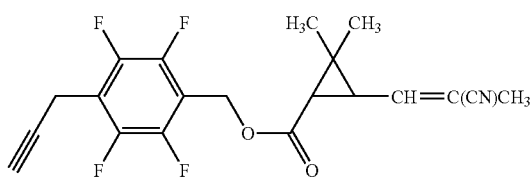

(1)

(hereinafter, referred to as the present compound), a pest controlling agent comprising the present compound as an active ingredient, and a method for controlling pests by applying an effective amount of the present compound to pests or a place where pests inhabit.

MODE OF CARRYING OUT THE INVENTION

There are isomers of the present compound, originated from two asymmetric carbon atoms on the cyclopropane ring, and from the double bond. The present invention includes each active isomer and an active mixture of the isomers at any ratio thereof.

Examples of the existing form of the present compound include those described below:

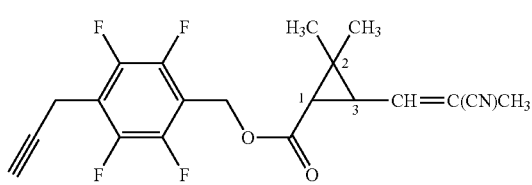

(1)

a compound of the formula (1), in which the absolute configuration of 1-position of the cyclopropane ring is the R-configuration;

a compound of the formula (1), in which the relative configuration of the substituents at 1-position and at 3-position of the cyclopropane ring is the trans configuration;

a compound of formula (1), in which the relative configuration of the substituents at 1-position and at 3-position of the cyclopropane ring is the cis configuration;

a compound of formula (1), in which the relative configuration of the double bond of the substituent at 3-position of the cyclopropane ring is the Z-configuration;

a compound of formula (1), in which the absolute configuration of 1-position of the cyclopropane ring is the R-configuration and the relative configuration of the substituents at 1-position and at 3-position of the cyclopropane ring is the trans configuration;

a compound of formula (1), in which the absolute configuration of 1-position on the cyclopropane ring is the R-configuration and the relative configuration of the substituents at 1-position and at 3-position of the cyclopropane ring is the cis configuration;

a compound of formula (1), in which the absolute configuration of 1-position on the cyclopropane ring is R-configuration, the relative configuration of the substituents at 1-position and at 3-position of the cyclopropane ring is the trans configuration and the relative configuration of the double bond of the substituent at 3-position of the cyclopropane ring is the Z-configuration;

a compound of formula (1), in which the absolute configuration of 1-position on the cyclopropane ring is the R-configuration, the relative configuration of the substituents at 1-position and at 3-position of the cyclopropane ring is the cis configuration and the relative configuration of the double bond of the substituent at 3-position of the cyclopropane ring is the Z-configuration;

a compound of formula (1) rich in an isomer, in which the absolute configuration of 1-position on the cyclopropane ring is the R-configuration and the relative configuration of the substituents at 1-position and at 3-position of the cyclopropane ring is the trans configuration;

a compound of formula (1) containing 80% or more of an isomer, in which the absolute configuration of 1-position on the cyclopropane ring is the R-configuration and the relative configuration of the substituents at 1-position and at 3-position of the cyclopropane ring is the trans configuration; and a compound of formula (1) containing 90% or more of an isomer, in which the absolute configuration of 1-position on the cyclopropane ring is the R-configuration and the relative configuration of the substituents at 1-position and at 3-position of the cyclopropane ring is the trans configuration.

The present compound can be prepared, for example, by the following production method. The method reacting an alcohol compound represented by the formula (2)

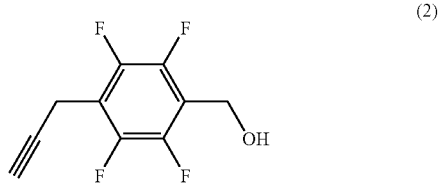

(2)

with a carboxylic acid compound represented by the formula (3)

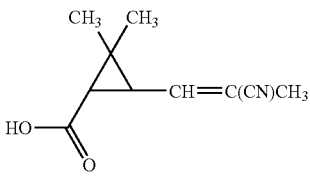

or a reactive derivative thereof (e.g., acid halide, acid anhydride, etc.).

This reaction is usually carried out in a solvent in the presence of a condensing agent or a base.

Examples of the condensing agent include dicyclohexylcarbodiimide and 1-(3-dimethylaminopropyl)-3-ethylcarbodiimide hydrochloride.

Examples of the base include organic bases such as triethylamine, pyridine, N,N-diethylaniline, 4-dimethylaminopyridine, diisopropylethylamine, etc.

Examples of the solvent include hydrocarbons such as benzene, toluene, hexane, etc.; ethers such as diethyl ether, tetrahydrofuran, etc.; halogenated hydrocarbons such as dichloromethane, 1,2-dichloroethane, chlorobenzene, etc.; and the like.

The reaction time is usually within the range of 5 minutes to 72 hours.

The reaction temperature is usually within the range of −20° C. to 100° C. (provided that, when a solvent used has a boiling point below 100° C., −20° C. to the boiling point of the solvent), preferably −5° C. to 100° C. (provided that, when a solvent used has a boiling point below 100° C., −5° C. to the boiling point of the solvent).

The reaction can be carried out at any molar ratio of the alcohol compound of the formula (2) to the carboxylic acid compound of the formula (3) or a reactive derivative thereof, but preferably at a ratio of one mole to one mole or around this ratio.

The condensing agent or the base can be used in any ratio usually in the range of one mole to an excess amount, preferably one to five moles, relative to one mole of the alcohol compound of the formula (2). The condensing agent or the base is appropriately selected depending on a particular kind of the carboxylic acid compound of the formula (3) or a reactive derivative thereof.

After the reaction has been completed, the present compound can be isolated by carrying out a conventional post-treatment operation such as filtration of a reaction mixture, followed by concentrating the filtrate, or to pour a reaction mixture into water, followed by extracting with an organic solvent and concentrating the extract. The isolated present compound can be further purified by chromatography, distillation, or the like.

The alcohol compound of the formula (2) is described, for example, in EP 0196156 A1, and can be prepared according to the method described therein.

The carboxylic acid compound of the formula (3) is described, for example, in Agr. Biol. Chem., 34, 1119 (1970) and can be prepared according to the method described therein.

Examples of pests controlled by the present compound include arthropods such as insects, acarines, and the like. Specific examples are those described below.

Lepidoptera:
Pyralid moths (Pyralidae) such as rice stem borer (*Chilo suppressalis*), rice leafroller (*Cnaphalocrocis medinalis*), Indian meal moth (*Plodia interpunctella*), and the like, owlet moths (Noctuidae) such as common cutworm (*Spodoptera litura*), rice armyworm (*Pseudaletia separata*), cabbage armyworm (*Mamestra brassicae*), and the like, whites (Pieridae) such as common cabbageworm (*Pieris rapae*), and the like, tortricid moths (Tortricidae) such as *Adoxophyes orana*, and the like, Carposimidae, lyonetiid moths (Lyonetiidae), tussock moths (Lymantriidae), *Autographa*, *Agrotis* spp. such as cutworm (*Agrotis segetum*), black cutworm (*Agrotis ipsilon*), and the like, *Helicoverpa* spp., *Heliothis* spp., diamondback (*Plutella xylostella*), rice skipper (*Parnara guttata*), casemaking clothes moth (*Tinea pellionella*), webbing clothes moth (*Tineola bisselliella*), and the like;

Diptera:
Mosquitos (Calicidae) such as common mosquito (*Culex pipiens pallens*), *Culex tritaeniorhynchus*, and the like, *Aedes* spp. such as *Aedes aegypti*, *Aedes albopictus*, and the like, *Anopheles* such as *Anopheles sinensis* and the like, midges (Chironomidae), house flies (Muscidae) such as housefly (*Musca domestica*), false stablefly (*Muscina stabulans*), lesser housefly (*Fannia canicularis*), and the like, Calliphoridae, Sarcophagidae, anthomyiid flies (Anthomyiidae) such as seedcorn maggot (*Hylemya platura*), onion maggot (*Delia antiqua*), and the like, fruit flies (Tephritidae), small fruit flies (Drosophilidae), moth flies (Psychodidae), Phoridae, black flies (Simuliidae), Tabanidae, stable flies (Stomoxyidae), Ceratopogonidae, and the like;

Blattodea:
German cockroach (*Blattella germanica*), smokybrown cockroach (*Periplaneta fuliginosa*), American cockroach (*Periplaneta americana*), brown cockroach (*Periplaneta brunnea*), oriental cockroach (*Blatta orientalis*) and the like;

Hymenoptera:
Ants (Formicidae), hornets, yellow jackets and potter wasps (Vespidae), bethylid wasps, sawflies (Tenthredinidae) such as cabbage sawfly (*Athalia rosae japonensis*), and the like;

Aphaniptera:
*Ctenocephalides canis*, *Ctenocephalides felis*, *Pulex irritans* and the like;

Anoplura:
*Pediculus humanus*, *Phthirus pubis*, *Pediculus humanus humanus*, *Pediculus humanus corporis*, and the like;

Isoptera:
*Reticulitermes speratus*, *Coptotermes formosanus*, and the like;

Hemiptera:
Planthoppers (Delphacidae) such as small brown planthopper (*Laodelphax striatellus*), brown rice planthopper (*Nilaparvata lugens*), white-backed rice planthopper (*Sogatella furcifera*), and the like, leafhoppers (Deltocephalidae) such as green rice leafhopper (*Nephotettix cincticeps*), green rice leafhopper (*Nephotettix virescens*), and the like, aphids (Aphididae), stink bugs (Pentatomidae), whiteflies (Aleyrodidae), scales (Coccidae), lace bugs (Tingidae), psyllids (Psyllidae), and the like;

Coleoptera:
Corn rootworm (*Diabrotica* spp.) such as *Attagenus japonicus*, *Anthrenus verbasci*, western corn rootworm (*Diabrotica virgifera*), southern corn rootworm (*Diabrotica*

*undecimpunctata howardi*), and the like, scarabs (Scarabaeidae) such as cupreous chafer (*Anomala cuprea*), soybeen beetle (*Anomala rufocuprea*), and the like, weevils (Curculionidae) such as maize weevil (*Sitophilus zeamais*), rice water weevil (*Lissorhoptrus oryzophilus*), cottonseed weevil (*Anthonomus gradis gradis*), adzuki been weevil (*Callosobruchuys chienensis*), and the like, darkling beetles (Tenebrionidae) such as yellow mealworm (*Tenebrio molitor*), red flour beetle (*Tribolium castaneum*), and the like, leaf beetles (Chrysomelidae) such as rice leaf beetle (*Oulema oryzae*), striped flea beetle (*Phyllotreta striolata*), cucurbit leaf beetle (*Aulacophora femoralis*), and the like, drugstore beetles (Anobiidae), *Epilachna* spp. such as twewnty-eight-spotted ladybird (*Epilachna vigintioctopunctata*), and the like, powder post beetles (Lyctidae), false powder post beetles (Bostrychidae), longhorn beetles (Cerambycidae), rove beetle (*Paederus fuscipes*), and the like;

Thysanoptera:

*Thrips palmi, Frankliniella occidentalis*, flower thrips (*Thrips hawaiiensis*), and the like;

Orthoptera:

Mole crickets (Gryllotalpidae), grasshoppers (Acrididae), and the like;

Acarina:

House dust mites (Epidermoptidae) such as *Dermatophagoides farinae, Dermatophagoides ptrenyssnus*, and the like, acarid mites (Acaridae) such as mold mite (*Tyrophagus putrescentiae*), brown legged grain mite (*Aleuroglyphus ovatus*), and the like, Glycyphagidae such as *Glycyphagus privatus, Glycyphagus domesticus*, groceries mite (*Glycyphagus destructor*), and the like, cheyletid mites (Cheyletidae) such as *Cheyletus malaccensis, Cheyletus fortis*, and the like, Tarsonemidae, Chortoglyphidae, Haplochthoniidae, spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and the like; and hard ticks (Ixodidae) such as *Haemaphysalis longicornis*, and the like.

The pest controlling agent of the present invention may be the present compound itself or, usually, may be a formulation of the present compound.

Examples of the formulation include oil solutions, emulsifiable concentrates, wettable powders, flowable formulations (e.g. aqueous suspension and aqueous emulsion), dusts, granules, aerosols, volatile formulations by heating (e.g. mosquito-coil, mosquito-mat for electric heating and volatile formulations with absorptive wick for heating), heating fumigants (e.g. self-burning type fumigants, chemical reaction type fumigants and porous ceramic plate fumigant), non-heating volatile formulations (e.g. resin volatile formulations and impregnated paper volatile formulations), smoking formulations (e.g. fogging), ULV formulations and poisonous baits.

The formulation can be prepared, for example, by the following methods:

(1) mixing the present compound with a liquid and/or gaseous carrier, and optionally adding a surfactant and other auxiliaries for a formulation;

(2) mixing the present compound with a powdery solid carrier, and optionally adding a surfactant and other auxiliaries for a formulation; and (3) impregnating a shaped solid carrier with the present compound; or mixing the present compound with a powdery solid carrier, and optionally adding a surfactant and other auxiliaries for a formulation, and shaping the resulting mixture.

A content of the present compound depends on a particular type of formulations but, usually, these formulations can contain 0.001 to 95% by weight of the present compound.

Examples of the carrier used for the formulation include solid carriers such as clays (e.g. kaolin clay, diatomaceous earth, synthetic hydrated silicon oxide, bentonite, Fubasami clay and acid clay), talc and the like, ceramics, other inorganic minerals (e.g. sericite, quartz, sulfur, active carbon, calcium carbonate, hydrated silicon oxide and montmorillonite) and chemical fertilizers (e.g. ammonium sulfate, ammonium phosphate, ammonium nitrate, urea and ammonium chloride); liquid carriers such as water, alcohols (e.g. methanol and ethanol), ketones (e.g. acetone and methyl ethyl ketone), aromatic hydrocarbons (e.g. benzene, toluene, xylene, ethylbenzene, methylnaphthalene and phenylxylylethane), aliphatic hydrocarbons (e.g. hexane, cyclohexane, kerosene and gas oil), esters (e.g. ethyl acetate and butyl acetate), nitrites (e.g. acetonitrile and isobutyronitrile), ethers (e.g. diisopropyl ether and dioxane), acid amides (e.g. N,N-dimethylformamide and N,N-dimethylacetamide), halogenated hydrocarbons (dichloromethane, trichloroethane and carbon tetrachloride), dimethyl sulfoxide and vegetable oils (e.g. soybean oil and cottonseed oil); and gaseous carriers such as chlorofluorocarbon gas, butane gas, LPG (liquefied petroleum gas), dimethyl ether and carbon dioxide gas.

Examples of the surfactant include alkyl sulfate esters, alkylsulfonate salts, alkylarylsulfonate salts, alkyl aryl ethers, polyoxyethylenated alkyl aryl ethers, polyethylene glycol ethers, polyhydric alcohol esters and sugar alcohol derivatives.

Examples of the other auxiliaries for a formulation include sticking agents, dispersing agents and stabilizers, typically casein, gelatin, polysaccharides (e.g. starch, gum arabic, cellulose derivatives and alginic acid), lignin derivatives, bentonite, synthetic water-soluble polymers (e.g. polyvinyl alcohol and polyvinylpyrrolidone), polyacrylic acid, BHT (2,6-di-tert-butyl-4-methylphenol) and BHA (mixture of 2-tert-butyl-4-methoxyphenol and 3-tert-butyl-4-methoxyphenol).

Examples of the solid carrier for a mosquito-coil include a mixture of raw plant powder such as wood powder and Pyrethrum marc and a binding agent such as Tabu powder (powder of *Machilus thunbergii*), starch or gluten.

Examples of the shaped solid carrier for a mosquito-mat for electric heating include plates of compacted fibrils of cotton linters and of a mixture of pulp and cotton linters.

Examples of the solid carrier for the self-burning type fumigant includes exothermic combustion agents such as nitrate, nitrite, guanidine salt, potassium chlorate, nitrocellulose, ethylcellulose and wood powder, pyrolytic stimulating agents such as alkali metal salts, alkaline earth metal salts, dichromates and chromates, oxygen sources such as potassium nitrate, combustion assistants such as melanin and wheat starch, bulk fillers such as diatomaceous earth and binding agents such as synthetic glue.

Examples of the solid carrier for a chemical reaction type fumigant include exothermic agents such as alkali metal sulfides, polysulfides, hydrogensufides and calcium oxide, catalytic agents such as carbonaceous substances, iron carbide and activated clay, organic foaming agents such as azodicarbonamide, benzenesulfonyl hydrazide, dinitrosopentamethylene tetramine, polystyrene and polyurethane and fillers such as natural and synthetic fibers.

Examples of the solid carrier for a non-heating volatile formulation include thermoplastic resins and paper such as filter paper and Japanese paper.

Examples of the base material for a poisonous bait include bait ingredients such as grain powder, vegetable oil, sugar and crystalline cellulose, antioxidants such as dibutyl hydroxytoluene and nordihydroguaiaretic acid, preservatives such as dehydroacetic acid, substances for preventing children and pets from erroneous eating such as red pepper powder, pest-attractant flavorants such as cheese flavorant, onion flavorant and peanut oil.

The method for controlling pests of the present invention is usually carried out by applying the pest controlling agent of the present invention containing an effective amount of the present compound to pests or a place where pests inhabit.

The formulation of the pest controlling agent of the present invention is applied, for example, by the following methods:

(1) applying the formulation as such to pests or a place where pests inhabit;

(2) spraying the formulation in the form of a diluted solution with a solvent such as water to pests or a place where pests inhabit; in this case, a concentration of the active ingredient in the diluted solution is usually 0.1 to 10000 ppm, or (3) volatilizing the active ingredient by heating the formulation at a place where pests inhabit.

These methods can be appropriately selected according to a particular type of the agent, application place, or the like.

In any method, the amount of the present compound to be applied can be appropriately determined according a particular form of the pest controlling agent of the present invention, time, place and method of the application, kind of the pests, damage, and the like. Usually, when applied on a plane, the amount is 1 to 10,000 mg per 1 m$^2$, and when applied in a space, the amount is 0.1 to 5,000 mg per 1 m$^3$.

The pest controlling agent of the present invention can be used together with or by mixing with other insecticides, nematocides, fungicides, herbicides, plant growth regulators, repellents, synergists, fertilizers and/or soil conditioners.

Examples of the active ingredients of the insecticide and acaricide include:

organophosphorus compounds such as fenitrothion, fenthion, diazinon, chlorpyrifos, acephate, methidathion, disulfoton, DDVP, sulprofos, cyanophos, dioxabenzofos, dimethoate, phenthoate, malathion, trichlorfon, azinphosmethyl, monocrotophos and ethion;

carbamate compounds such as BPMC, benfuracarb, propoxur, carbosulfan, carbaryl, methomyl, ethiofencarb, aldicarb, oxamyl and fenothiocarb;

pyrethroid compounds such as etofenprox, fenvalerate, esfenvalerate, fenpropathrin, cypermethrin, permethrin, cyhalothrin, deltamethrin, cycloprothrin, fluvalinate, bifenthrin, 2-methyl-2-(4-bromodifluoromethoxyphenyl)propyl (3-phenoxybenzyl)ether, tralomethrin, silafluofen, d-phenothrin, cyphenothrin, d-resmethrin, acrinathrin, cyfluthrin, tefluthrin, transfluthrin, tetramethrin, allethrin, d-furamethrin, prallethrin, empenthrin and 5-(2-propynyl)furfuryl 2,2,3,3-tetramethylcyclopropanecarboxylate;

nitroimidazolidine derivatives; N-cyanoamidine derivatives such as acetamiprid; chlorinated hydrocarbon compounds such as endosulfan, γ-BHC and 1,1-bis(chlorophenyl)-2,2,2-trichloroethanol; benzoylphenylurea compounds such as chlorfluazuron, teflubenzuron and flufenoxuron; phenylpyrazole compounds; metoxadiazon; bromopropylate; tetradifon; chinomethionat; pyridaben; fenpyroximate; diafenthiuron; tebufenpyrad; polynactins complex such as tetranactin, dinactin and trinactin; pyrimidifen; milbemectin; abamectin; ivermectin; and azadirachtin.

Examples of the repellent include 3,4-caranediol, N,N-diethyl-m-toluamide, 1-methylpropyl 2-(2-hydroxyethyl)-1-piperidinecarboxylate, p-menthan-3,8-diol, botanical essential oils such as hyssop oil, and the like.

Examples of the synergist include bis(2,3,3,3-tetrachloropropyl)ether (S-421), N-(2-ethylhexyl)bicyclo[2.2.1]hept-5-ene-2,3-dicarboximide (MGK-264) and 5-((2-(2-Butoxyethoxy)ethoxy)methyl)-6-propyl-1,3-benzodioxole (piperonyl butoxide).

The present invention will be further illustrated in detail by the following Production Example, Formulation Examples and Test Examples.

First, the Production Example of the present compound will be described.

PRODUCTION EXAMPLE

Under nitrogen atmosphere, to a mixture of 0.20 g of 4-propargyl-2,3,5,6-tetrafluorobenzyl alcohol, 0.17 g of (1R)-trans-3-(2-cyano-1-propenyl)-2,2-dimethylcyclopropanecarboxylic acid, 0.022 g of 4-dimethylaminopyridine in 7 ml of dichloromethane was added 0.21 g of N,N-dicyclohexylcarbodiimide, and the mixture was stirred at room temperature for three hours. Then, the reaction mixture was filtrated, and the filtrate was concentrated under reduced pressure. The resultant residue was subjected to silica gel column chromatography to obtain 0.26 g of 4-propargyl-2,3,5,6-tetrafluorobenzyl (1R)-trans-3-(2-cyano-1-propenyl)-2,2-dimethylcyclopropanecarboxylate (hereinafter, referred to as the present compound (A)) represented by the formula (A):

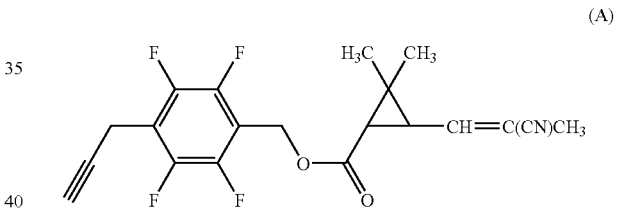

(an isomer ratio based on the double bond of the 2-cyano-1-propenyl group: Z/E=about 2/1).

$^1$H-NMR (CDCl$_3$, TMS) δ (ppm): 1.21 (s, 3H, Z+E forms), 1.32 (s, 3H, Z+E forms), 1.72 (t, 1H, Z+E forms), 1.96 (s, 3H, Z+E forms), 2.06 (s, 1H, Z+E forms), 2.20 (m, ⅓H, E form), 2.47 (m, ⅔H, Z form), 3.64 (s, 2H, Z+E forms), 5.24 (s, 2H, Z+E forms), 5.78 (d, ⅔H, Z form), 6.00 (d, ⅓H, E form)

Next, Formulation Examples will be described. Parts are by weight.

Formulation Example 1

To a solution of 20 parts of the present compound (A) in 65 parts of xylene is added 15 parts of Sorpol 3005X (registered trademark of Toho Chemical Industry Co., LTD.), and the mixture is thoroughly mixed with stirring to obtain an emulsifiable concentrate.

Formulation Example 2

To 40 parts of the present compound (A) is added 5 parts of Sorpol 3005X, and the mixture is thoroughly mixed with stirring. To the mixture are added 32 parts of Carplex #80 (synthetic hydrated silica, registered trademark of Shionogi & Co., Ltd.) and 23 parts of 300-mesh diatomaceous earth, and the resulting mixture is thoroughly mixed with a juice mixer to obtain a wettable powder.

Formulation Example 3

A mixture of 1.5 parts of the present compound (A), 1 part of Tokusil GUN (synthetic hydrated silica, manufactured by Tokuyama Corp.), 2 parts of Reax 85A (sodium ligninsulfonate, manufactured by Westvaco chemicals), 30 parts of Bentonite Fuji (bentonite, manufactured by Hojun Co.) and 65.5 parts of Shokozan A clay (kaolin clay, manufactured by Shokozan Kogyosho Co.) is thoroughly pulverized. To the resulting mixture is added water, and the mixture is kneaded, granulated with a piston-granulator and dried to obtain a 1.5% granule.

Formulation Example 4

A mixture of 10 parts of the present compound (A), 10 parts of phenylxylylethane and 0.5 part of Sumidur L-75 (tolylenediisocyanate manufactured by Sumika Bayer Urethane Co., Ltd.) is added to 20 parts of 10% aqueous solution of gum arabic, and stirred with a homomixer to obtain an emulsion having a mean particle diameter of 20 μm. To this is added 2 parts of ethylene glycol, and stirred for 24 hours on a water bath at 60° C. to obtain microcapsule slurry. On the other hand, 0.2 part of xanthan gum and 1.0 part of Veegum R (aluminum magnesium silicate manufactured by Sanyo Chemical Co., Ltd.) are dispersed in 56.3 parts of ion-exchanged water to obtain a thickener solution. A microencapsulated formulation is obtained by mixing 42.5 parts of the above microcapsule slurry and 57.5 parts of the thickener solution.

Formulation Example 5

A mixture of 10 parts of the present compound (A) and 10 parts of phenylxylylethane is added to 20 parts of 10% aqueous solution of polyethylene glycol, and the mixture is stirred with a homomixer to obtain an emulsion having a mean particle diameter of 3 μm. On the other hand, 0.2 part of xanthan gum and 1.0 part of Veegum R (aluminum magnesium silicate manufactured by Sanyo Chemical Co., Ltd.) are dispersed in 58.8 parts of ion-exchanged water to give a thickener solution. A flowable formulation is obtained by mixing 40 parts of the above emulsion and 60 parts of the thickener solution.

Formulation Example 6

A mixture of 5 parts of the present compound (A), 3 parts of Carplex #80 (fine powder of synthetic hydrated silicon dioxide, trademark of Shionogi & Co., Ltd.), 0.3 part of PAP (mixture of monoisopropyl phosphate and diisopropyl phosphate) and 91.7 parts of 300-mesh talc are stirred with a juice mixer to obtain a dust.

Formulation Example 7

A solution of 0.1 part of the present compound (A) in 10 parts of dichloromethane is mixed with 89.9 parts of deodorized kerosene to obtain an oil solution.

Formulation Example 8

A solution of 1 part of the present compound (A), 5 parts of dichloromethane and 34 parts of deodorized kerosene is filled in an aerosol vessel. A valve is attached to the vessel and 60 parts propellant (liquefied petroleum gas) is charged under pressure through the valve to obtain an oily aerosol.

Formulation Example 9

A solution of 0.6 part of the present compound (A), 5 parts of xylene, 3.4 parts of deodorized kerosene and 1 part of Atmos 300 (emulsifier, trademark of Atlas Chemical Co.) and 50 parts of water are filled in an aerosol vessel. A valve is attached to the vessel and 40 parts propellant (liquefied petroleum gas) is charged under pressure through the valve to obtain an aqueous aerosol.

Formulation Example 10

A solution of 0.3 g of the present compound (A) in 20 ml of acetone is uniformly mixed with 99.7 g of a base material for a mosquito-coil (mixture of Tabu powder, Pyrethrum marc and wood powder at the ratio of 4:3:3). To the mixture is added 100 ml of water and the resulting mixture is thoroughly kneaded, then molded and dried to obtain a mosquito-coil.

Formulation Example 11

A solution is prepared by adding acetone to 0.8 g of the present compound (A) and 0.4 g of piperonyl butoxide and adjusting to 10 ml. A base material (a plate of compacted fibrils of a mixture of pulp and cotton linter: 2.5 cm×1.5 cm, 0.3 cm of thickness) is uniformly impregnated with 0.5 ml of the above solution to obtain a mosquito-mat for electric heating.

Formulation Example 12

A solution of 3 parts of the present compound (A) in 97 pars of deodorized kerosene is filled in a container made of polyvinyl chloride. Into the container is inserted an absorptive wick made of inorganic powder solidified with a binder and then calcined, whose upper portion can be heated with a heater, to obtain a part of a absorptive wick type electric heating fumigation device.

Formulation Example 13

A porous ceramic plate (4.0 cm×4.0 cm, 1.2 cm of thickness) is impregnated with a solution of 100 mg of the present compound (A) in an appropriate amount of acetone to obtain a fumigant for heating.

Formulation Example 14

A solution of 100 μg of the present compound (A) in an appropriate amount of acetone is uniformly applied on a filter paper strip (2.0 cm×2.0 cm, 0.3 mm of thickness). Then, acetone is vaporized to obtain a volatile agent for using at room temperature.

The following Test Examples will show that the present compound is useful as an active ingredient for pest controlling agents.

Test Example 1

A solution of 0.025 part of the present compound (A) in 10 parts of dichloromethane was mixed with 89.975 parts of deodorized kerosene to obtain a 0.025% oil solution.

Adult houseflies (5 males and 5 females) were left in a cubic chamber (70 cm at each side). Into the chamber, 0.7 ml of 0.025% oil solution of the present compound (A) prepared above was sprayed with a spray gun at a pressure of $8.8\times10^4$ Pa from a small window on the side of the chamber. Two minutes after spraying, the number of the knocked-down insects was counted (repeated twice).

The same test was carried out except that 4-propargyl-2,3,5,6-tetrafluorobenzyl (1R)-trans-3-(2-methyl-1-propenyl)-2,2-dimethylcyclopropanecarboxylate represented by the formula:

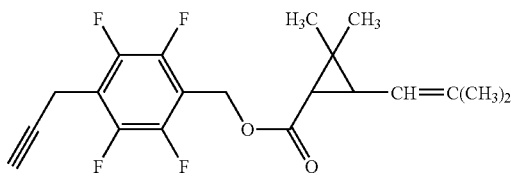

(The compound described as compound 2 in TABLE 1 of EP 0196156 A1; hereinafter, referred to as the comparative compound 1) was used instead of the present compound (A).

Knock-down ratios, i.e., ratios of the number of knocked-down insects 2 minutes after the spraying to the number of tested insects, are shown in Table 1.

TABLE 1

| Test compound | Knock-down ratio (%) |
|---|---|
| Present compound (A) | 100 |
| Comparative compound 1 | 0 |

Test Example 2

A solution of 0.00625 part of the present compound (A) in 10 parts of dichloromethane was mixed with 89.99375 parts of deodorized kerosene to obtain a 0.00625% oil solution.

Adult houseflies (5 males and 5 females) were left in a cubic chamber (70 cm at each side). Into the chamber, 0.7 ml of 0.00625% oil solution of the present compound (A) prepared above was sprayed into the chamber with a spray gun at a pressure of $8.8\times10^4$ Pa from a small window on the side of the chamber. Then, up to 10 minutes after spraying, the number of the knocked-down insects was counted with time (repeated twice). The time required for knocking down 90% of the tested insects ($KT_{90}$) was calculated from the results.

The same tests were carried out except for using the comparative compound 1 and 4-methoxymethyl-2,3,5,6-tetrafluorobenzyl (1R)-trans-3-(2-cyano-1-propenyl)-2,2-dimethylcyclopropanecarboxylate represented by the formula:

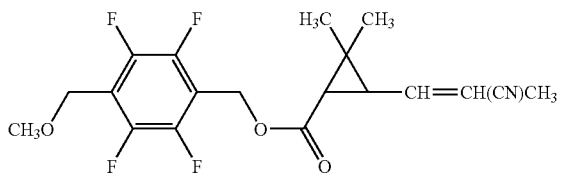

(The compound described in JP 2004-2363 A; hereinafter, referred to as the comparative compound 2.).

The results are shown in Table 2.

TABLE 2

| Test compound | $KT_{90}$ (minutes) |
|---|---|
| Present compound (A) | 2.0 |
| Comparative compound 1 | Not less than 10 |
| Comparative compound 2 | 4.3 |

INDUSTRIAL APPLICABILITY

The present compound is useful as an active ingredient for a pest controlling agent.

The invention claimed is:

1. An ester compound represented by the formula (1):

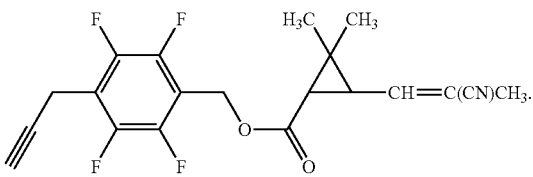

(1)

2. A pest controlling agent comprising the ester compound of the formula (1) according to claim 1 as an active ingredient.

3. A method for controlling pests which comprises applying an effective amount of the ester compound of the formula (1) according to claim 1 to pests or a place where pests inhabit.

* * * * *